United States Patent
Chen et al.

(10) Patent No.: US 9,624,183 B2
(45) Date of Patent: Apr. 18, 2017

(54) PROCESS FOR THE PREPARATION OF A FLUOROLACTON DERIVATIVE

(71) Applicant: Gilead Pharmasset LLC, Foster City, CA (US)

(72) Inventors: Rongmin Chen, Zhejiang (CN); Yuanqiang Li, Zhejiang (CN); Jianqiang Zhao, Zhejiang (CN); Jianbing Zheng, Zhejiang (CN); Guoliang Zhu, Zhejiang (CN)

(73) Assignee: Gilead Pharmasset LLC, Foster City, CA (US)

( * ) Notice: Subject to any disclaimer, the term of this patent is extended or adjusted under 35 U.S.C. 154(b) by 8 days.

(21) Appl. No.: 14/798,879

(22) Filed: Jul. 14, 2015

(65) Prior Publication Data

US 2015/0315165 A1 Nov. 5, 2015

Related U.S. Application Data

(63) Continuation of application No. PCT/EP2014/050439, filed on Jan. 13, 2014.

(30) Foreign Application Priority Data

Jan. 14, 2013 (WO) ................. PCT/CN2013/070413

(51) Int. Cl.
*C07D 307/33* (2006.01)
*C07D 413/06* (2006.01)
*C07D 263/26* (2006.01)

(52) U.S. Cl.
CPC ......... *C07D 263/26* (2013.01); *C07D 307/33* (2013.01); *C07D 413/06* (2013.01); *Y02P 20/55* (2015.11)

(58) Field of Classification Search
None
See application file for complete search history.

(56) References Cited

U.S. PATENT DOCUMENTS

2008/0177079 A1 7/2008 Cedilote et al.

OTHER PUBLICATIONS

Office Action dated Jun. 3, 2016 for Chinese Application No. 2014800046681.

Written Opinion dated Apr. 21, 2016 for Singapore Application No. 11201505455V.
Zhou et al, "Synthesis of the alarm pheromone of the leaf-cutting and using (4S)-4-benzyl-oxazolidin-2-one as chiral auxiliary" Journal of Hubei University (Natural Science) 30(1):56-62 (Mar. 2008)—(Abstract in English).
Brunet et al., "Titanium mediated symmetric aldol reaction with α-fluoropropionimide enolates" Journal of Fluorine Chemistry, Elsevier 128:1271-1279 ( 2007).
Gaul et al., "Crystals structures—A manifesto for the superiority of the valine-derived 5,5-diphenyloxazolidinone as an auxiliary in enantioselective organic synthesis" Helvetica Chimica Acta 85:1546-1566 ( 2002).
ISR for PCT/EP2014/050439 (WO2014/108525).
Peddie et al., "Synthesis and conformation of fluorinated β-peptide compounds" Chemistry—A European Journal 18:6655-6662 ( 2012).
Zhang et al., "A practical synthesis of (2R)-3,5-di-O-benzoyl-2-fluoro-2-C-methyl-D-ribono-y-lactone" Tetrahedron Asymmetry 20(3):305-312 ( 2009).

*Primary Examiner* — Kamal Saeed
(74) *Attorney, Agent, or Firm* — Briana Barron

(57) ABSTRACT

A novel process for the preparation of a fluorolactone derivative of the formula

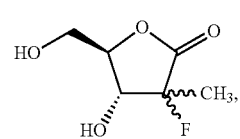

I and of its acylated derivative of formula

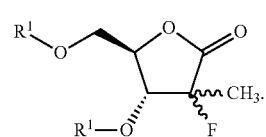

V wherein $R^1$ stands for a hydroxy protecting group is described.

The acylated fluorolactones of formula V, particularly the benzoyl derivative with $R^1$=benzyl are important precursors for the synthesis of prodrug compounds which have the potential to be potent inhibitors of the Hepatitis C Virus (HCV) NS5B polymerase.

16 Claims, No Drawings

PROCESS FOR THE PREPARATION OF A FLUOROLACTON DERIVATIVE

This application is a continuation of International Application PCT/EP2014/050439, filed Jan. 13, 2014, which claims the benefit of priority to International Application PCT/CN2013/070413, filed Jan. 14, 2013, each of which is incorporated herein by reference in its entirety.

The present invention relates to a novel process for the preparation of a fluorolactone derivative of the formula

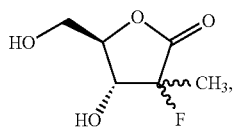

and of its acylated derivative of formula

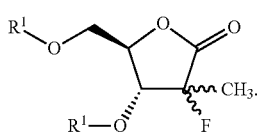

wherein $R^1$ stands for a hydroxy protecting group.

The acylated fluorolactones of formula V, particularly the benzoyl derivative with $R^1$=benzyl are important precursors for the synthesis of prodrug compounds which have the potential to be potent inhibitors of the Hepatitis C Virus (HCV) NS5B polymerase (PCT Int. Publ. WO 2007/065829).

Object of the present invention was to find a selective and scalable synthesis for the preparation of the fluorolactone of formula I and its acylated derivatives of formula V.

The object could be achieved with the synthesis of the present invention as described below.

The process of the present invention comprises the preparation of a fluorolactone derivative of the formula

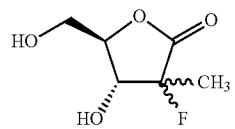

comprising the steps
a) reacting the aldehyde of the formula

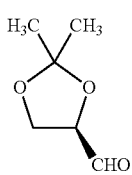

with a fluoropropionate derivative of formula

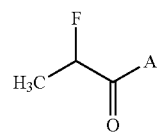

wherein A is selected from the chiral moieties and Ph stands for phenyl to form an aldol adduct of the formula wherein A is as above; and
b) subjecting to hydrolysis the aldol adduct of formula IV to give the fluorolactone derivative of the formula I.

The term "hydroxy protecting group" used for substituent $R^1$ refers to any substituents conventionally used to hinder the reactivity of the hydroxy group. Suitable hydroxy protecting groups are described in Green T., "Protective Groups in Organic Synthesis", Chapter 1, John Wiley and Sons, Inc., 1991, 10-142 and can e.g. be selected from benzyl, acetyl, trimethyl silyl, tert-butyl, tert-butyl dimethyl silyl or dihydropyranyl, but particularly benzyl.

The wave line " ⌇ " indicates a chiral bond, " ▬ " or " ▬ ".

Step a)
Step a) requires the reaction of the aldehyde of the formula II with a fluoropropionate derivative of formula III to form an aldol adduct of the formula IV.

D-glyceraldehyde acetonide is the aldehyde of formula II and commercially available.

The fluoropropionate derivatives of formula III can be prepared by converting 2-fluoropropionic chloride with e.g. butyl lithium in tetrahydrofuran at temperatures between −50° C. and −10° C. following the scheme below

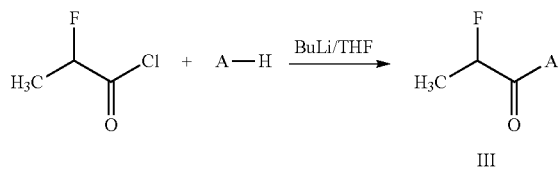

The chiral amines A-H, wherein A is selected from the chiral moieties

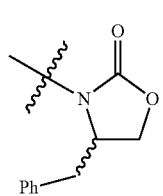
A1

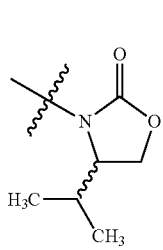
A2

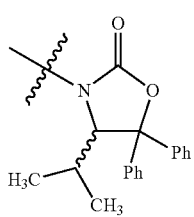
A3 are either commercially available or can be prepared according to the following schemes:

Scheme 1a (A—H with A = A1)

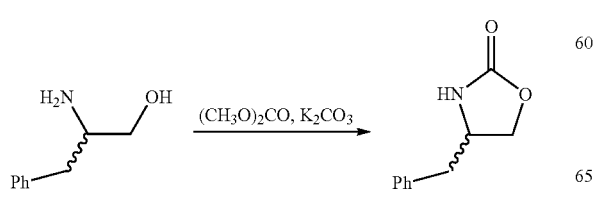

Scheme 1b: (A—H with A = A2)

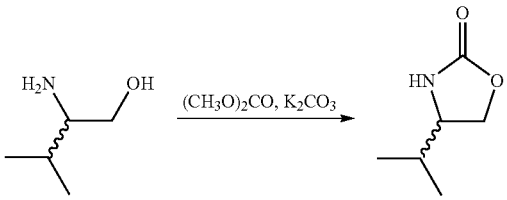

Scheme 1c: (A—H with A = A3

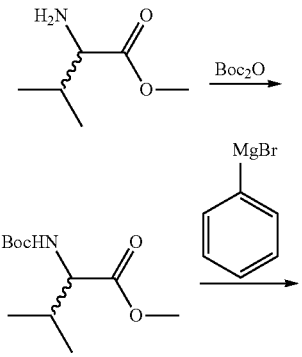

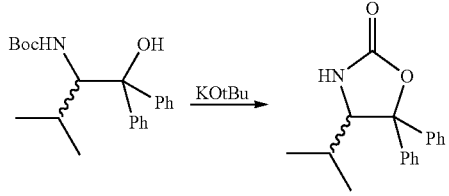

In a particular embodiment the fluoropropionate derivative of formula III wherein A is A3 is used.

In a more particular embodiment the substituent A in the fluoropropionate derivative of formula III is selected from the chiral moieties

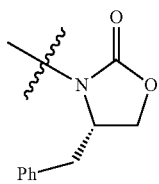
A1a

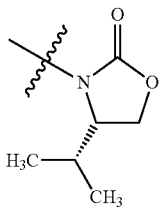
A2a

-continued

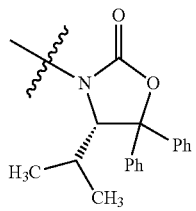
A3a even more particularly from A3a.
The fluoropropionate derivatives of formula III

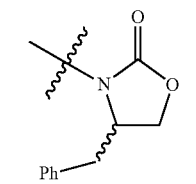
III wherein A is selected from the chiral moieties

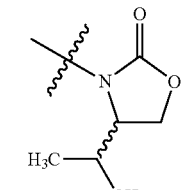
A1

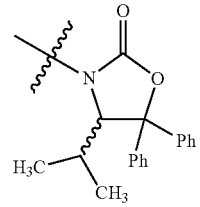
A2

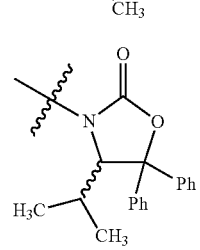
A3 wherein Ph stands for phenyl have so far have not been described in the art and therefore represent particular embodiments of the present invention.
In a more particular fluoropropionate derivative of formula III A is selected from

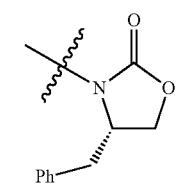
A1a

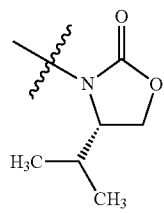
A2a

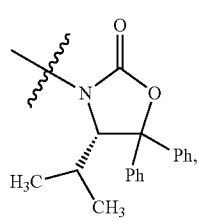
A3a even more particularly from A3a.

The reaction is performed in the presence of a catalyst selected from dibutylboron trifluormethanesulfonate, titanium chloride, titanium(IV) trichloride isopropoxide, titanium isopropoxide, magnesium chloride, magnesium triflate or zinc chloride.

Particularly dibutylboron trifluormethanesulfonate is used.

As a rule a base such as a tertiary amine selected from 2,6-lutidine, 2,3-lutidine, 2,4-lutidine, 2,5-lutidine, 3,4-lutidine, 3,5-lutidine, triethyl amine, diisopropylethyl amine, diethylamine, pyridine or 1,6-dimethylpyridine and a suitable organic solvent such as methylene chloride, 1,2-dichloroethane, chloroform, acetonitrile, toluene, xylene, chlorobenzene, tetrahydrofuran, 2-methyl tetrahydrofuran or methyl isobutylether, or mixtures thereof are present.

A particularly suitable tertiary amine is 2,6-lutidine and a particularly suitable organic solvent is methylene chloride.

The reaction temperature is usually held between −78° C. and 50° C.

The resulting aldol adduct of formula IV can be obtained from the reaction mixture applying methods known to the skilled in the art, particularly by adding water to the reaction mixture, by separating the organic phase and removing the solvent. Further purification can be achieved by crystallization from a methylene chloride solution with hexane.

The aldol adducts of formula IV are not known in the art and therefore represent particular embodiments of the present invention.

More particular the aldol adducts have the formula

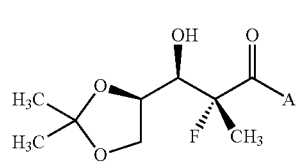
IVa wherein the chiral moiety A is as above and selected from A1, A2 or A3, more particular from A1a, A2a or A3a and even more particular from A3a.

Step b)

Step b) requires subjecting to hydrolysis the aldol adduct of formula IV to give the fluorolactone derivative of the formula I.

In a particular embodiment the aldol adduct of the formula IVa with the preferences as outlined above is used resulting in the fluorolactone derivative of the formula

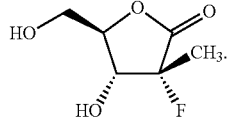
Ia

The hydrolysis is as a rule performed with an oxidizing agent selected from hydrogen peroxide, meta-chloroperoxybenzoic acid, sodium hypochlorite, sodium perchlorate or ethylene oxide in the presence of an alkali hydroxide selected from lithium-, sodium- or potassium hydroxide as base.

Hydrogen peroxide is usually selected as a suitable oxidizing agent and an aqueous solution of lithium hydroxide is particularly used as base.

The hydrolysis is usually performed at reaction temperatures between −30° C. and 50° C.

It is a particular embodiment of the present invention that the chiral moieties A are cleaved off with the hydrolysis and can be recovered in the form of the respective chiral amine A-H of the formulae

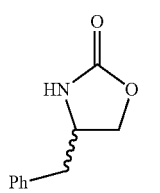
A11

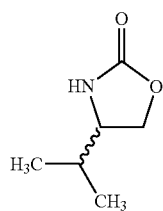
A12

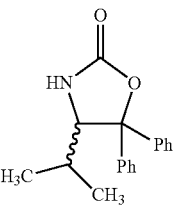
A13 or more particularly of the formulae

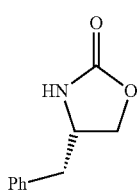
A11a

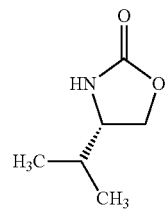
A12a

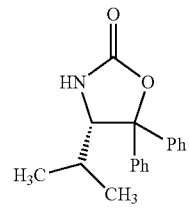
A13a

The chiral amine A-H can be isolated and recovered from the reaction mixture by methods known to the skilled in the art, e.g. in case of the chiral amine A13a by simply filtering it off rom the reaction mixture.

In a further particular embodiment of the invention the fluorolactone derivative of the formula I is acylated to form the acylated fluorolactone of the formula

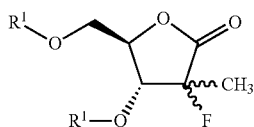
V wherein $R^1$ stands for a hydroxy protecting group.

The acylation is performed with a suitable acylating agent selected from benzoyl chloride, acetyl chloride, pivaloyl chloride, trimethylsilyl chloride, tert-butyl dimethylsilyl chloride or 3,4-dihydro-2H-pyran, particularly benzoyl chloride in the presence of a tertiary amine, such as with triethylamine, diisopropylethylamine, 2,3-lutidine, 2,4-lutidine, 2,5-lutidine, 3,4-lutidine, 3,5-lutidine, pyridine, 1,6-dimethylpyridine or 1,8-Diazabicyclo[5.4.0]undec-7-ene or mixtures thereof, particularly with triethylamine.

Usually 4-(Dimethylamino)-pyridine is added as catalyst.

A suitable organic solvent such as tetrahydrofuran, 2-methyl tetrahydrofuran, dichloromethane, 1,2-dichloroethane, acetonitrile, toluene, xylene, methyl isobutylketone, methyl tert-butylether or acetone, but particularly tetrahydrofuran is be present and the reaction temperatures is as a rule maintained between −20° C. and 80° C.

In a particular embodiment the acylated fluorolactone has the formula

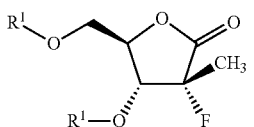
Va wherein $R^1$ stands for a hydroxy protecting group.

Suitable hydroxy protecting group $R^1$ is benzyl, acetyl, trimethyl silyl, tert-butyl, tert-butyl dimethyl silyl or dihydropyranyl, but particularly is benzyl.

The acylated fluorolactone can be isolated from the reaction mixture applying methods known to the skilled in the art, e.g. by extraction from the reaction mixture with a suitable organic solvent like methyl-tert.butyl ether and by removing the solvent.

EXAMPLES

Abbreviations
EA ethylacetate
HE hexane
MeOH methanol
THF tetrahydrofuran
TLC thin layer chromatography
Starting Materials

A. Preparation of (R)-2,2-dimethyl-1,3-dioxolane-4-carbaldehyde

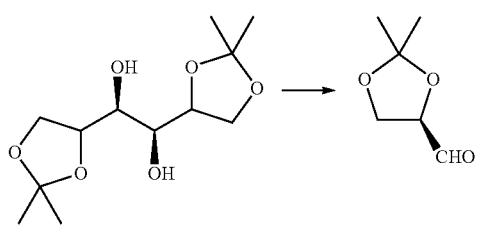

II

Methylene chloride (400 g), saturated NaHCO$_3$ solution (21 g), and (1S,2S)-1,2-bis(2,2-dimethyl-1,3-dioxolan-4-yl)ethane-1,2-diol (55 g, 0.21 mol) were added to a vessel. NaIO$_4$ (64 g, 0.30 mol) was added in 6 portions in 60 min., while maintaining the reaction temperature at 20-25° C. The reaction mixture was then stirred at 20-25° C. for 5 hrs, TLC check showed reaction completion. The reaction mixture was filtered to remove the solid, and the separated aqueous layer was extracted with methylene chloride (140 g). The combined organic layers were dried with anhydrous magnesium sulfate (40 g) at 0-5° C. for 3 hrs then filtered to remove Na$_2$SO$_4$ and rinsed with methylene chloride (50 g). The filtrate was concentrated under reduced pressure until dryness. The residue was distilled under reduced pressure and the fraction was collected at 40° C./1 Kpa. (R)-2,2-dimethyl-1,3-dioxolane-4-carbaldehyde (23 g, 0.18 mol, 42% yield) was obtained.

B. Preparation of Chiral Amines

B1. Preparation of (S)-4-benzyloxazolidin-2-one

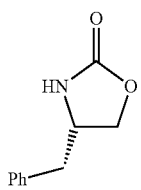

A11a (S)-phenylalanol (25 g, 0.17 mol), anhydrous potassium carbonate (2.3 g, 0.017 mol), and dimethyl carbonate (30 g, 0.33 mol) were added to a vessel. The mixture was heated to 80° C. The distillation receiver was cooled in an ice bath, and methanol (ca. 13.5 ml) was collected from the reaction mixture over 4.5 hrs. The oil bath was removed, when the distillation of methanol ceased. The light-yellow residue was cooled to ambient temperature, and diluted with 125 ml of ethyl acetate. The solution was transferred to a separation funnel, and washed with water (125 ml). The organic phase was dried over anhydrous magnesium sulfate, filtered, and concentrated with rotary evaporator, to afford a white crystalline solid. The crude solid was added into a hot solution of 2:1 ethyl acetate/hexane (100 ml), and filtered hot. The filtrate was allowed to come to r.t, and the solids crystallized from the solution to afford (S)-4-benzyloxazolidin-2-one (A11a) (23 g, 78.5% yield).

B2. Preparation of (S)-4-isopropyloxazolidin-2-one

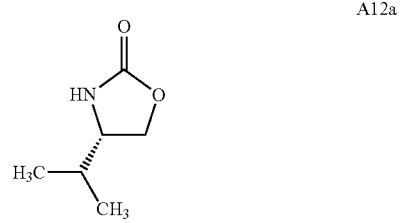

A12a

L-valinol (5 g, 48.5 mmol), anhydrous potassium carbonate (0.67 g, 4.85 mmol), and dimethyl carbonate (8.7 g, 96.7 mmoll) were added to a vessel. The mixture was heated to 80° C. The distillation receiver was cooled in an ice bath, and methanol (ca. 3.8 ml) was collected from the reaction mixture over 4.5 hrs. The oil bath was removed, when the distillation of methanol ceased. The light-yellow residue was cooled to ambient temperature, and diluted with 30 ml of ethyl acetate. The solution was transferred to a separation funnel, and washed with water (25 ml). The organic phase was dried over anhydrous magnesium sulfate, filtered, and concentrated with rotary evaporator, to afford a white crystalline solid. The crude solid was added into a hot solution of 1:1 ethyl acetate/hexane (20 ml), and filtered hot. The filtrate was allowed to come to r.t, and the solids crystallized from the solution to afford (S)-4-isopropyloxazolidin-2-one (A12a) (5.0 g, 80.0% yield).

B3. Preparation of (S)-4-isopropyl-5,5-diphenyloxazolidin-2-one

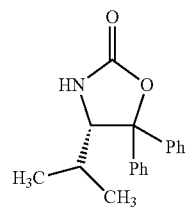

A13a

L-Valine methylester hydrochloride (50 g, 0.30 mol) and 200 g of methanol were added to a vessel. Triethylamine (37.5 ml, 0.27 mol) was charged and the reaction temperature was kept at <25° C. Then di-tert-butyl dicarbonate (68.3 g, 0.31 mol) was charged. After that, triethylamine (63.7 ml, 0.46 mol) was charged dropwise, while controlling the reaction temperature at <25° C. The mixture was stirred at 25° C. for 2 hrs until TLC showed no remaining starting material. Thereafter methanol was removed under reduced pressure. Methyl isobutyl ether (200 ml) was charged, followed by addition of water (150 ml) and then the mixture was stirred for 30 min. The layers were separated, the aqueous phase was extracted with methyl tert-butylether (100 ml). The combined organic phases were washed with NaCl solution (150 ml), dried with Na₂SO₄ (10 g), then filtered, and the filtrate was concentrated under reduced pressure until dryness. Boc-L-valine methylester (74.5 g) was obtained as crude product which could directly be used for the subsequent reaction.

Bromobenzene (158.6 g, 1.0 mol) and THF (500 mL) were charged into a vessel to prepare the bromobenzene/THF solution and filled in a adding funnel. Mg (27.1 g, 1.1 mol) and THF (100 mL) were charged into a flask, then ¹/₁₀ of the bromobenzene/THF solution and a small granule of I₂ were added and heated to 60° C. to initiate the reaction. The remaining bromobenzene/THF solution was charged at such a rate that a gentle refluxing of the reaction mixture could be maintained. Reflux was maintained for another 1 hr, then the reaction mixture was cooled to 0° C. A solution of Boc-L-valine methylester (74.5 g, 0.30 mol) in THF (75 mL) was then added dropwise while controlling the reaction temperature at ≤3° C. After addition, the solution was warmed to 20° C. within 1 hr and maintained at 20° C. for 15 hrs. After cooling to 0° C. a saturated NH₄Cl solution (200 mL) was charged, the mixture was then stirred for 30 min followed by phase separation. The aqueous phase was extracted with ethyl acetate (2×250 mL). The combined organic phases were washed with saturated NaCl solution (150 mL), dried with Na₂SO₄ (20 g) and filtered. The filtrate was concentrated to dryness under reduced pressure. Ethyl acetate (250 mL) was added to the residue, and the mixture was heated to reflux to dissolve the solid. Hexane (250 mL) was added at >60° C. and the mixture was then cooled down to 0° C. in 2 hrs and stirred at 0° C. for 1 hr. The solid was then separated by filtration, washed with 70 mL of hexane and dried under vacuum, to give the Boc-aminol ((S)-2-(Boc-amino)-3-methyl-1,1-diphenyl-1-butanol) in the form of a white solid (84 g). The mother liquor was concentrated to ca. 70 g. Then hexane (70 mL) was charged for crystallization. A 2$^{nd}$ crop of solid was collected by filtration and was washed with small amount of hexane. The solid was dried under vaccum and 12.5 g of solid was obtained.

Boc-aminol (96 g, 0.27 mol) and THF (1500 mL) were charged in a vessel and the mixture was cooled to 0° C. Potassium tert butoxide (36.3 g, 0.32 mol) was charged in one portion and the mixture was stirred at 0° C. for 3 hrs. Upon completion (TLC check) the reaction mixture was poured into a 10% NH₄Cl solution (2000 mL), and stirred for 10 min. The solid was filtered off, rinsed with water (4×400 mL) and then dissolved in methanol (500 mL). The solution was heated to reflux for 1 hr, then cooled to 15~20° C., and stirred for 1 hr. The suspension was filtered and the cake was washed with methanol (100 mL). The solid was dried under vacuum at 38° C. and 75 g (S)-4-isopropyl-5,5-diphenyloxazolidin-2-one (A13a) was obtained.

C. Preparation of Fluoropropionates of Formula III

C1. (4S)-3-(2-fluoropropanoyl)-4-benzylloxazolidin-2-one (Formula III with A=A1a)

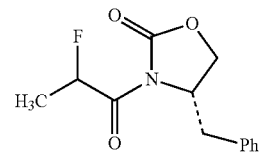 [SMILES: CC(F)C(=O)N1C(=O)OC[C@@H]1Cc1ccccc1]

(S)-4-Benzyloxazolidin-2-one (10 g, 0.056 mol) and THF (200 ml) were charged to a vessel. The solution was cooled to −70° C., then n-butyllithium solution 2.7 M (27.5 ml, 0.074 mol) was added dropwise, while maintaining the reaction temperature at <−70° C. The reaction mixture was then stirred for 30 min., then 2-fluoropropionic chloride (10.1 g, 0.095 mol) was added dropwise, while maintaining the reaction temperature at <−70° C. Then the reaction mixture was warmed to 15~20° C. within 3 hrs followed by stirring at 15~20° C. for further 60 min. Upon reaction completion, 10% NH₄Cl solution (60 ml) was added and the mixture was stirred for 30 min. Phases were separated and the aqueous phase was extracted with methyl tert-butylether (30 ml). The combined organic layers were washed with saturated NaCl solution, dried with Na₂SO₄, filtered and evaporated under reduced pressure to remove the solvents. The residue was purified by column chromatography (eluent: HE/EA=3/1 v/v) to obtain 4S)-3-(2-fluoropropanoyl)-4-benzylloxazolidin-2-one (12.1 g, 85% yield) as a light yellow oil.

¹H-NMR (CDCl₃, 400 MHz): δ7.28 (m, 5H), 6.05 (m, 1H), 4.74 (m, 1H), 4.31 (m, 2H), 4.39 (m, 1H), 2.87 (m, 1H), 1.65 (m, 3H).

C2. (4S)-3-(2-fluoropropanoyl)-4-isopropyloxazolidin-2-one (Formula III with A=A2a)

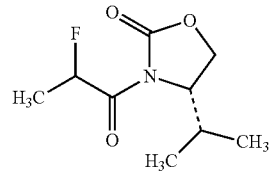

(S)-4-Isopropyloxazolidin-2-one (3.8 g, 0.029 mol) and THF (75 ml) were charged to a vessel. The solution was cooled to −60° C., then n-butyllithium solution 2.7 M (18 ml, 0.049 mol) was added dropwise, while maintaining the reaction temperature at <−50° C. The reaction mixture was then stirred at −50° C. for 30 min, then 2-fluoropropionic chloride (6.3 g, 0.057 mol) was added dropwise, while maintaining the reaction temperature at <−50° C. The reaction temperature was then raised to 15~20° C. within 3 hrs. followed by stirring at 15~20° C. for further 60 min. Upon reaction completion, 10% NH₄Cl solution (30 ml) was charged and the reaction mixture was stirred for 30 min. Phases were separated and the aqueous phase was extracted with methyl tert-butylether (30 ml). The combined organic layers were washed with saturated NaCl solution (30 ml). The organic phase was dried with Na₂SO₄, filtered and evaporated under reduced pressure to remove the solvents. The residue was purified by column chromatography (eluent: HE/EA=3/1 v/v) to obtain (4S)-3-(2-fluoropropanoyl)-4-isopropyloxazolidin-2-one (2.9 g, 48% yield) as a light yellow oil.

$^1$H-NMR (CDCl$_3$, 400 MHz): δ6.00 (m, 1H), 4.39 (m, 3H), 2.43 (m, 1H), 1.61 (m, 3H), 0.91 (m, 6H).

C3. (4S)-3-(2-fluoropropanoyl)-4-isopropyl-5,5-diphenyloxazolidin-2-one (Formula III with A=A3a)

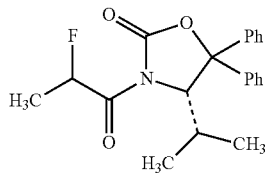 [SMILES: CC(F)C(=O)N1C(=O)OC(c2ccccc2)(c2ccccc2)[C@@H]1C(C)C]

(S)-4-isopropyl-5,5-diphenyloxazolidin-2-one (70 g, 0.25 mol) and THF (500 mL) were charged to a vessel. The solution was cooled to −50° C., then n-butyllithium solution 2.5 M (120 mL, 0.30 mol) was added dropwise while maintaining the reaction temperature at <−40° C. After addition, the reaction temperature was raised to −10° C. within 3 hrs., and stirred at −10° C. for 30 min. the reaction mixture was cooled to −78° C., 2-fluoropropionic chloride (41 g, 0.37 mol) added dropwise at such a rate that the reaction temperature was maintained at <−60° C. After addition, the reaction mixture was warmed to 15~20° C. in 3 hrs., and stirred at 15~20° C. for 60 min. 10% NH$_4$Cl solution (350 mL) was charged and the mixture stirred for 30 min. Phases were separated and the aqueous one extracted with methyl tert-butylether (500 mL). The combined organic layers were washed with saturated NaCl solution (150 ml). The organic phase was dried with Na$_2$SO$_4$, filtered and evaporated under reduced pressure to remove the solvents. The residue was dissolved in methylene chloride (70 mL) by warming up the mixture then 210 mL hexane was added within 30 min. The suspension was cooled to 0° C. in 2 hrs. and stirred at 0° C. for 60 min. The suspension was filtered and the solid dried under vacuum. (4S)-3-(2-fluoropropanoyl)-4-isopropyl-5,5-diphenyloxazolidin-2-one (74.5 g, 84.2% yield) was obtained in the form of a light yellow solid $^1$H-NMR (CDCl$_3$, 400 MHz): δ7.36 (m, 10H), 5.96 (m, 1H), 5.49 (d, J=3.2 Hz, 0.5H), 5.31 (d, J=3.2 Hz, 0.5H), 2.02 (m, 1H), 1.73 (dd, J=23.6, 6.8 Hz, 1.5H), 1.15 (dd, J=23.6, 6.8 Hz, 1.5H), 0.83 (m, 6H).

D. Preparation of Aldol Adduct of Formula IV

D1. (S)-3-((2R,3R)-3-((R)-2,2-dimethyl-1,3-dioxolan-4-yl)-2-fluoro-3-hydroxy-2-methylpropanoyl)-4-benzyloxazolidin-2-one (Formula IV with A=A1a)

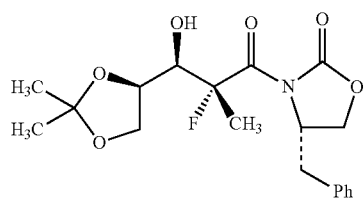 [SMILES: CC1(C)OC[C@H]([C@@H](O)[C@@](C)(F)C(=O)N2C(=O)OC[C@@H]2Cc2ccccc2)O1]

(4S)-3-(2-Fluoropropanoyl)-4-benzyloxazolidin-2-one (2.9 g, 0.0115 mol) and methylene chloride (20 ml) were charged to a vessel and the mixture was cooled to 0° C. Dibutylboron trifluormethanesulfonate (Bu$_2$BOTf, 1 M in CH$_2$Cl$_2$), (17.3 ml, 0.0173 mol) was charged and the reaction mixture was stirred at 0° C. for 10 min. Then 2,6-lutidine (2.47 g, 0.0231 mol) was added, while maintaining the reaction temperature at 0° C. for 15 min. Thereafter the reaction mixture was warmed up to 15~20° C. and stirred for 4 hrs. The mixture was then cooled to −78° C., thereafter 2,3-O-isopropylidene-D-glyceradehyde (2.25 g, 0.0173 mol) was added dropwise, while maintaining the reaction temperature at <−65° C. Then the mixture was warmed up to 0° C. in 5 hrs and further stirred at 0° C. for another 1 hr. Water (30 ml) was added, the mixture was stirred for 30 min, then the layers were separated. The organic layer was washed with water (30 ml), dried with Na$_2$SO$_4$ (10 g), filtered and concentrated at reduced pressure to remove the solvent. The residue was purified by column chromatography (eluent: HE/EA=3/1 v/v), to give the title product (S)-3-((2R,3R)-3-((R)-2,2-dimethyl-1,3-dioxolan-4-yl)-2-fluoro-3-hydroxy-2-methylpropanoyl)-4-benzyloxazolidin-2-one (3.5 g, 79.5% yield) as a light yellow oil.

$^1$H-NMR (CDCl$_3$, 400 MHz): δ7.29 (m, 5H), 4.63 (m, 2H), 4.22 (m, 4H), 4.04 (dd, J=8, 6.4 Hz, 1H), 3.56 (dd, J=13.2, 2.8 Hz, 1H), 2.65 (dd, J=13.2, 10.8 Hz, 1H), 1.86 (d, J=23.2 Hz, 3H), 1.42 (s, 3H), 1.33 (s, 3H).

D2. (S)-3-((2R,3R)-3-((R)-2,2-dimethyl-1,3-dioxolan-4-yl)-2-fluoro-3-hydroxy-2-methylpropanoyl)-4-isopropyloxazolidin-2-one (Formula IV with A=A2a)

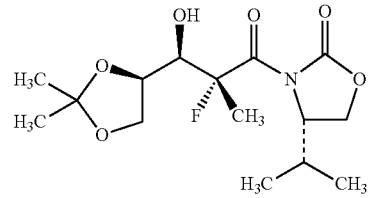 [SMILES: CC(C)[C@H]1COC(=O)N1C(=O)[C@](C)(F)[C@H](O)[C@H]1COC(C)(C)O1]

(4S)-3-(2-Fluoropropanoyl)-4-isopropyloxazolidin-2-one (1.5 g, 7.4 mmol) and methylene chloride (20 ml) were charged to a vessel and the mixture was cooled to 0° C. Dibutylboron trifluormethanesulfonate (Bu$_2$BOTf, 1 M in CH$_2$Cl$_2$), (11.0 ml, 11 mmol) was charged and the reaction mixture was stirred at 0° C. for 10 min. Then 2,6-lutidine (1.6 g, 14.9 mmol) was added, while maintaining the reaction temperature at 0° C. for 15 min. Thereafter the reaction mixture was warmed up to 15~20° C. and stirred for 4 hrs. The mixture was then cooled to −78° C., thereafter 2,3-O-isopropylidene-D-glyceradehyde (1.5 g, 11.5 mol) was added dropwise, while maintaining the reaction temperature at <−65° C. Then the mixture was warmed up to 0° C. in 5 hrs and further stirred at 0° C. for another 1 hr. Water (16 ml) was added, the mixture was stirred for 30 min then the layers were separated. The organic layer was washed with water (16 ml), dried with Na$_2$SO$_4$ (10 g), filtered and concentrated at reduced pressure to remove the solvent. The residue was purified by column chromatography (eluent: HE/EA=3/1 v/v), to give the title product (S)-3-((2R,3R)-3-((R)-2,2-dimethyl-1,3-dioxolan-4-yl)-2-fluoro-3-hydroxy-2-methylpropanoyl)-isopropyloxazolidin-2-one (2.2 g, 89.8% yield) as light yellow oil.

¹H-NMR (CDCl₃, 400 MHz): δ4.50 (m, 1H), 4.46 (m, 1H), 4.35 (m, 1H), 4.28 (m, 1H), 4.20 (m, 1H), 4.10 (m, 1H), 4.01 (m, 1H), 2.94 (d, J=6.4 Hz, 1H), 2.45 (m, 1H), 1.81 (d, J=23.2 Hz, 3H), 1.40 (s, 3H), 1.35 (s, 3H), 0.96 (m, 6H).

D3. (S)-3-((2R,3R)-3-((R)-2,2-dimethyl-1,3-dioxolan-4-yl)-2-fluoro-3-hydroxy-2-methylpropanoyl)-4-isopropyl-5,5-diphenyloxazolidin-2-one (Formula IV with A=A3a)

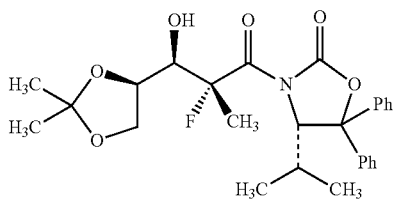 [SMILES: CC(C)[C@@H]1N(C(=O)[C@](C)(F)[C@H](O)[C@H]2COC(C)(C)O2)C(=O)OC1(c1ccccc1)c1ccccc1]

(4S)-3-(2-Fluoropropanoyl)-4-isopropyl-5,5-diphenyloxazolidin-2-one (90 g, 0.25 mol) and methylene chloride (720 ml) was charged to a vessel and the mixture was cooled to 0° C. Dibutylboron trifluormethanesulfonate (Bu₂BOTf, 1 M in CH₂Cl₂), (378 ml, 0.38 mol) was charged and the reaction mixture was stirred at 0° C. for 10 min. Then 2,6-Lutidine (55.8 g, 0.52 mol) was added, while maintaining the reaction temperature at 0° C. for 15 min. Thereafter the reaction mixture was warmed up to 15~20° C. and stirred at this temperature for 24 hrs. The mixture was then cooled to −78° C., thereafter, 2,3-O-isopropylidene-D-glyceradehyde (54.6 g, 0.42 mol) was added dropwise, while maintaining the reaction temperature at <−65° C. Then the mixture was warmed up to 0° C. in 5 hrs and stirred at 0° C. for another 1 hr. Water (450 ml) was added, the mixture was stirred for 30 min, then the layers were separated. The organic layer was washed with water (450 ml), dried with Na₂SO₄, filtered and concentrated at reduced pressure to remove the solvent. The residue was dissolved in methylene chloride (90 ml) upon heating to reflux. Then hexane (270 ml) was added dropwise for iniating crystallization. The suspension was cooled to 10° C. in 2 hrs, stirred at 10° C. for 1 hr, filtered and the filter cake was washed with hexane (90 ml) and dried under vacuum. (S)-3-((2R,3R)-3-((R)-2,2-dimethyl-1,3-dioxolan-4-yl)-2-fluoro-3-hydroxy-2-methylpropanoyl)-4-isopropyl-5,5-diphenyloxazolidin-2-one was obtained in a yield of 79 g (64.3%).

¹H-NMR (CDCl₃, 400 MHz): δ7.38 (m, 10H), 5.30 (d, J=3.2 Hz, 1H), 4.63 (m, 1H), 4.00 (dd, J=12.8, 6.4 Hz, 1H), 3.68 (m, 1H), 3.70 (m, 1H), 2.20 (d, J=6.8 Hz, 1H), 1.47 (d, J=23.2 Hz, 3H), 1.39 (s, 3H), 1.33 (s, 3H), 0.98 (d, J=7.2 Hz, 3H), 0.86 (d, J=6.8 Hz, 3H).

Example 1

Preparation of (3R,4R)-3-fluoro-4-hydroxy-5-(hydroxymethyl)-3-methyldihydrofuran-2(3H)-one (from aldol adduct of Example D1)

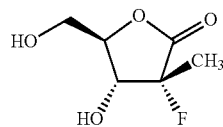

(S)-3-((2R,3R)-3-((R)-2,2-dimethyl-1,3-dioxolan-4-yl)-2-fluoro-3-hydroxy-2-methylpropanoyl)-4-benzyloxazolidin-2-one (3.3 g, 0.0086 mol), THF (10 ml) and water (2 ml) were charged to a vessel, and the solution was cooled to 0° C. Hydrogen peroxide 50% (2.36 g, 0.035 mol) was added, followed by a solution of lithium hydroxide monohydrate (0.3 g, 0.014 mol) in water (15 ml) while maintaining the reaction temperature at <5° C. The mixture was then stirred at 0~5° C. for 1 hr. Upon completion of the reaction (TLC check) a solution of sodium sulfite (5.50 g) in water (60 ml) was added at <10° C. The pH of the reaction mixture was adjusted to 6.5~7.0 by adding 10% HCl aqueous solution. THF was then removed under reduced pressure and methylene chloride (20 ml) was then added to the residue. The layers were separated, the water layer was extracted with methylene chloride (20 ml) and the aqueous layer was evaporated under reduced pressure to dryness. THF (20 ml) was added to the residue and the solids were filtered. The filter cake was rinsed with THF (10 ml) and the combined filtrates were concentrated to dryness. The residue was again taken up in THF (20 ml) and the mixture was stirred for 30 min and filtered. The filter cake was again rinsed with THF (10 ml) and the combined filtrates were concentrated under reduced pressure to dryness. Then ethanol (15 ml) and 0.3 ml HCl (0.3 ml) was added to the residue and the mixture was warmed up to 70° C. and stirred for 5 hrs. The mixture was concentrated until dryness, and was purified by column chromatography (eluent: CH₂Cl₂/MeOH=1/1 v/v), the title product (1.2 g) was collected and crystallized from CH₂Cl₂/MeOH=20/1 v/v to get the pure title product (3R,4R)-3-fluoro-4-hydroxy-5-(hydroxymethyl)-3-methyldihydrofuran-2(3H)-one (1.0 g, 70% yield).

¹H-NMR (D₂O, 400 MHz): δ4.55 (m, 1H), 4.19 (dd, J=21.2, 7.6 Hz, 1H), 4.04 (dd, J=13.2, 1.6 Hz, 1H), 3.81 (dd, J=13.2, 4.8 Hz, 1H), 1.62 (d, J=24.4 Hz, 3H).

Example 2

Preparation of (3R,4R)-3-fluoro-4-hydroxy-5-(hydroxymethyl)-3-methyldihydrofuran-2(3H)-one (from aldol adduct of example D2)

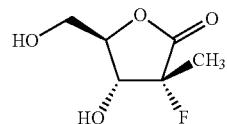

(S)-3-((2R,3R)-3-((R)-2,2-Dimethyl-1,3-dioxolan-4-yl)-2-fluoro-3-hydroxy-2-methylpropanoyl)-4-isopropyloxazolidin-2-one (2.2 g, 0.0066 mol, THF (10 ml) and water (2 ml) were charged to a vessel and the solution was cooled to 0° C. Hydrogen peroxide 50% (1.75 g, 0.026 mol) was added, followed by a solution of lithium hydroxide monohydrate (0.2 g, 0.011 mol) in water (10 ml) while maintaining the reaction temperature at <5° C. The mixture was then stirred at 0~5° C. for 1 hr. Upon completion of the reaction (TLC check) a solution of sodium sulfite (3.6 g) in water (35 ml) was added at <10° C. The pH of the reaction mixture was adjusted to 6.5~7.0 by adding 10% HCl aqueous solution. THF was then removed under reduced pressure and methylene chloride (15 ml) was then added to the residue. The layers were separated, the water layer was extracted with methylene chloride (20 ml) and the aqueous layer was evaporated under reduced pressure to dryness. THF (15 ml)

was added to the residue and the solids were filtered. The filtered cake was rinsed with THF (10 ml) and the combined filtrates were concentrated to dryness. The residue was again taken up in THF (20 ml) and the mixture was stirred for 30 min and filtered. The filtered cake was again rinsed with THF (10 ml) and the combined filtrates were concentrated under reduced pressure to dryness. Then ethanol (15 ml) and 0.3 ml HCl (0.3 ml) was added to the residue and the mixture was warmed up to 70° C. and stirred for 5 hrs. The mixture was concentrated until dryness, and was purified by column chromatography (eluent: $CH_2Cl_2$/MeOH=1/1 v/v), the title product (3R,4R)-3-fluoro-4-hydroxy-5-(hydroxymethyl)-3-methyldihydrofuran-2(3H)-one (0.72 g, 67% yield) was collected.

Example 3

Preparation of (3R,4R)-3-fluoro-4-hydroxy-5-(hydroxymethyl)-3-methyldihydrofuran-2(3H)-one (from aldol adduct of example D3)

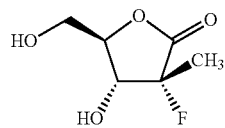

(S)-3-((2R,3R)-3-((R)-2,2-Dimethyl-1,3-dioxolan-4-yl)-2-fluoro-3-hydroxy-2-methylpropanoyl)-4-isopropyl-5,5-diphenyloxazolidin-2-one (75 g, 0.155 mol) THF (375 ml) and water (95 g) were charged to a vessel and the solution was cooled to 0° C. Hydrogen peroxide 50% (42 ml, 0.62 mol) was added followed by a solution of lithium hydroxide monohydrate (10.39 g, 0.25 mol) in water (100 ml) while maintaining the reaction temperature at <5° C. The mixture was then stirred at 0~5° C. for 1 hr. Upon completion of the reaction (TLC check) a solution of sodium sulfite (120 g, 0.95 mol) in water (600 ml) was added at <10° C. The pH of the reaction mixture was adjusted to 6.5~7.0 by adding 10% HCl aqueous solution. The reaction mixture was filtered and the filter cake (=chiral amine of formula A13a; see recovery example below) was washed with water (75 ml). THF was then removed from the filtrate under reduced pressure and methylene chloride (375 ml) was then added to the residue and the mixture was stirred for 30 min. The layers were separated, the water layer was extracted with methylene chloride (375 ml) and the aqueous layer was evaporated under reduced pressure to dryness. (for work up of organic layer see recovery example below). The residue was taken up in ethanol (150 ml), the mixture was stirred for 30 min. and filtered. The filter cake was washed with ethanol (25 ml) and the combined filtrates were concentrated to dryness. The residue was again taken up in ethanol (75 ml), the mixture was stirred for 30 min and filtered. The filter cake was washed with ethanol (15 ml) and the combined filtrates were concentrated under reduced pressure to dryness. The residue was then dissolved in THF (75 ml), insoluble solids were filtered off and the filtrate was concentrated to dryness. This procedure was repeated three times. (3R,4R)-3-fluoro-4-hydroxy-5-(hydroxymethyl)-3-methyldihydrofuran-2(3H)-one (25.5 g, 100% yield) could be obtained which was without further purification used for the benzylation step.

Recovery of (S)-4-isopropyl-5,5-diphenyloxazolidin-2-one (=chiral amine of formula A13a The wet cake (see above) was taken up in water (375 ml), the mixture was stirred for 30 min, filtered and the filter cake was washed twice with water (100 ml×2). The wet cake was dried under vacuum at 50° C. for 24 hrs to get a white solid (35.2 g). The organic layer (see above) was evaporated under reduced pressure to dryness and the residue was taken up in methanol (25 ml), filtered and washed with methanol (5 ml). The wet cake was dried under vacuum at 50° C. for 24 hrs to give a white solid (6.3 g). The total recovered chiral amine was 41.5 g=95% recovery yield.

Example 4

Preparation of ((3R,4R)-3-(benzoyloxy)-4-fluoro-4-methyl-5-oxotetrahydrofuran-2-yl)methyl benzoate

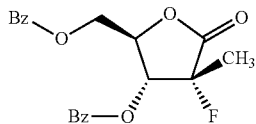

(3R,4R)-3-fluoro-4-hydroxy-5-(hydroxymethyl)-3-methyldihydrofuran-2(3H)-one (25.5 g, 0.155 mol) obtained from example 3 was dissolved in 200 ml of THF. 4-(Dimethylamino)-pyridine (8.3 g, 0.067 mol) and triethylamine (35 g, 0.35 mol) were added and the reaction mixture was cooled to 0° C. Benzoyl chloride (46.7 g, 0.33 mol) was added, and the mixture was warmed to 35~40° C. in the course of 2 hrs. Upon completion of the reaction (TLC check) water (100 ml) was charged and the mixture was stirred for 30 min. Phases were separated and to the aqueous phase methyl-tert-butyl ether (100 ml) was added and the mixture was stirred for 30 min. Phases were separated and the organic phase was washed with saturated NaCl solution (100 ml). The combined organic phases were dried over $Na_2SO_4$ (20 g) filtered and the filtrate was evaporated to dryness. The residue was taken up in i-propanol (250 ml) and the mixture was warmed to 50° C. and stirred for 60 min, then cooled down to 0° C. and further stirred for 60 min. The solid was filtered and the wet cake was washed with i-propanol (50 ml) and then dried under vacuum. The title compound ((3R,4R)-3-(benzoyloxy)-4-fluoro-4-methyl-5-oxotetrahydrofuran-2-yl)methyl benzoate (48.3 g, 83.9% yield) was obtained.

$^1$H-NMR (CDCl$_3$, 400 MHz): δ8.10 (d, J=7.6 Hz, 2H), 8.00 (d, J=7.6 Hz, 2H), 7.66 (t, J=7.6 Hz, 1H), 7.59 (t, J=7.6 Hz, 1H), 7.50 (m, 2H), 7.43 (m, 2H), 5.53 (dd, J=17.6, 5.6 Hz, 1H), 5.02 (m, 1H), 4.77 (dd, J=12.8, 3.6 Hz, 1H), 4.62 (dd, J=12.8, 5.2 Hz, 1H), 1.77 (d, J=23.2 Hz, 3H).

The invention claimed is:
1. Process for the preparation of a fluorolactone derivative of the formula

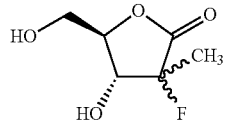

I comprising the steps
a) reacting the aldehyde of the formula

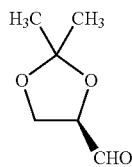   II with a fluoropropionate derivative of formula

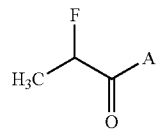   III wherein A is selected from the chiral moieties

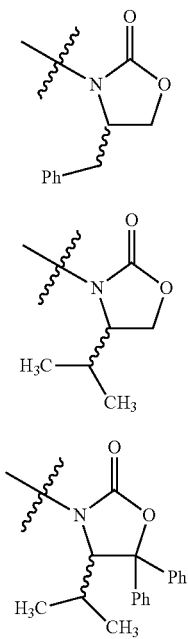

and Ph stands for phenyl to form an aldol adduct of the formula

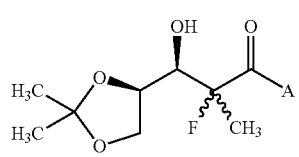   IV wherein A is as above; and
b) subjecting to hydrolysis the aldol adduct of formula IV to give the fluorolactone derivative of the formula I.

2. Process of claim 1, wherein the chiral moiety A in the fluoropropionate derivative of formula III is A3.

3. Process of claim 1, wherein the fluorolactone derivative has the formula

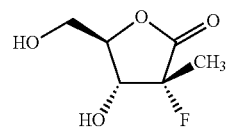   Ia and A is selected from the chiral moieties

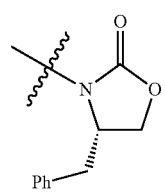   A1a

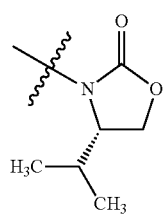   A2a

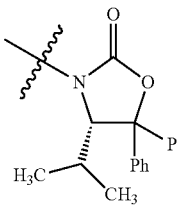   A3a and Ph is phenyl.

4. Process of claim 3, wherein the chiral moiety A in the fluoropropionate derivative of formula III is A3a.

5. Process of claim 1, wherein the fluorolactone derivative of formula I is acylated to form the acylated fluorolactone of formula

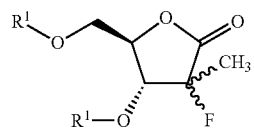   V wherein $R^1$ stands for a hydroxy protecting group.

6. Process of claim 5, wherein the acylated fluorolactone has the formula

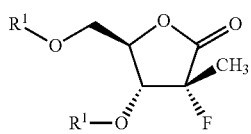

Va wherein R¹ stands for a hydroxy protecting group.

7. Process of claim 5, wherein the hydroxy protecting group R¹ stands for benzyl.

8. Process of claim 1, wherein the chiral moieties A can be recovered in the form of the respective chiral amines A-H of the formulae

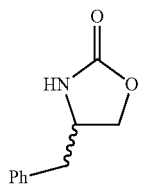

A11

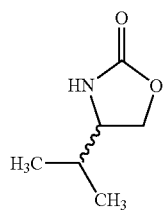

A12

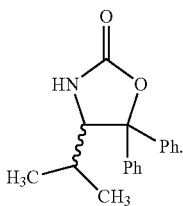

A13

9. Process of claim 1, wherein the reaction in step a) is performed in the presence of a catalyst selected from dibutylboron trifluormethanesulfonate, titanium chloride, titanium(IV) trichloride isopropoxide, titanium isopropoxide, magnesium chloride, magnesium triflate or zinc chloride.

10. Process of claim 9, wherein the catalyst is dibutylboron trifluormethanesulfonate.

11. Process of claim 1, wherein the reaction in step a) is performed in the presence of a base and an organic solvent at reaction temperatures between −78° C. and 50° C.

12. Process of claim 1, wherein the hydrolysis in step b) is performed with an oxidizing agent in the presence of an alkali hydroxide base.

13. Process of claim 12, wherein the hydrolysis in step b) is performed with hydrogen peroxide as oxidizing agent and lithium hydroxide as alkali hydroxide base.

14. Process of claim 1, wherein the hydrolysis in step b) is performed at reaction temperatures between −30° C. and 50° C.

15. Process of claim 5, wherein the acylation is performed in the presence of a tertiary amine at reaction temperatures between −20° C. and 80° C.

16. Process of claim 15 wherein the acylating agent is benzoyl chloride.

* * * * *